US010184058B2

(12) United States Patent
Mori

(10) Patent No.: US 10,184,058 B2
(45) Date of Patent: Jan. 22, 2019

(54) INK COMPOSITION FOR DETECTING PLASMA TREATMENT AND INDICATOR FOR DETECTING PLASMA TREATMENT

(71) Applicant: SAKURA COLOR PRODUCTS CORPORATION, Osaka-shi, Osaka (JP)

(72) Inventor: Marimo Mori, Osaka (JP)

(73) Assignee: SAKURA COLOR PRODUCTS CORPORATION, Osaka-shi (JP)

(*) Notice: Subject to any disclaimer, the term of this patent is extended or adjusted under 35 U.S.C. 154(b) by 0 days.

(21) Appl. No.: 15/305,822

(22) PCT Filed: Apr. 15, 2015

(86) PCT No.: PCT/JP2015/061545
§ 371 (c)(1),
(2) Date: Oct. 21, 2016

(87) PCT Pub. No.: WO2015/163203
PCT Pub. Date: Oct. 29, 2015

(65) Prior Publication Data
US 2017/0044389 A1    Feb. 16, 2017

(30) Foreign Application Priority Data

Apr. 21, 2014   (JP) .................. 2014-087638

(51) Int. Cl.
| C09D 11/50 | (2014.01) |
| C09D 11/037 | (2014.01) |
| C09D 11/10 | (2014.01) |
| C09D 11/102 | (2014.01) |
| A61L 2/14 | (2006.01) |
| A61L 2/28 | (2006.01) |
| B65D 5/42 | (2006.01) |
| B65D 25/54 | (2006.01) |
| B65D 75/52 | (2006.01) |
| B65D 81/20 | (2006.01) |
| B08B 7/00 | (2006.01) |
| H01J 37/32 | (2006.01) |
| H01L 21/3065 | (2006.01) |
| G01N 33/52 | (2006.01) |

(52) U.S. Cl.
CPC .............. C09D 11/50 (2013.01); A61L 2/14 (2013.01); A61L 2/28 (2013.01); C09D 11/037 (2013.01); C09D 11/10 (2013.01); C09D 11/102 (2013.01); G01N 33/52 (2013.01); H01L 21/3065 (2013.01)

(58) Field of Classification Search
CPC ....... C09D 11/50; C09D 11/037; C09D 11/10; C09D 11/102; A61L 2/114; A61L 2/28; B65D 5/4216; B65D 25/54; B65D 75/522; B65D 81/2084; H01J 37/32963; H01J 37/32972; B08B 7/0035

USPC ................... 106/31.32, 31.64; 436/1; 422/28
See application file for complete search history.

(56) References Cited

U.S. PATENT DOCUMENTS

| 4,155,895 A | * | 5/1979 | Rohowetz ................. A61L 2/28 |
| | | | 106/31.32 |
| 4,179,397 A | * | 12/1979 | Rohowetz ................. A61L 2/28 |
| | | | 106/31.32 |
| 4,839,311 A | | 6/1989 | Riley et al. |
| 5,955,025 A | | 9/1999 | Barrett |
| 5,990,199 A | * | 11/1999 | Bealing ..................... A61L 2/28 |
| | | | 106/31.13 |
| 6,063,631 A | | 5/2000 | Ignacio |
| 6,117,685 A | | 9/2000 | Omatsu et al. |
| 6,267,242 B1 | | 7/2001 | Nagata et al. |
| 6,355,448 B1 | | 3/2002 | Foltz et al. |
| 6,410,338 B1 | | 6/2002 | Lippold et al. |
| 6,524,763 B1 | | 2/2003 | Kuroda et al. |
| 6,852,281 B2 | | 2/2005 | Inoue et al. |
| 7,189,355 B2 | | 3/2007 | Mikumo et al. |
| 7,364,700 B2 | | 4/2008 | Maruo et al. |
| 7,364,770 B2 | | 4/2008 | Nagashima et al. |
| 7,976,781 B2 | | 7/2011 | Maruo et al. |
| 7,981,687 B2 | | 7/2011 | Yamaguchi et al. |
| 8,222,327 B2 | | 7/2012 | Mikumo et al. |
| 8,530,242 B2 | | 9/2013 | Lin et al. |
| 2001/0054374 A1 | | 12/2001 | Omatsu et al. |
| 2002/0051733 A1 | | 5/2002 | Antonoplos et al. |
| 2002/0121629 A1 | | 9/2002 | Mikumo et al. |
| 2005/0054374 A1 | | 3/2005 | Namiki |
| 2006/0194056 A1 | | 8/2006 | Nagashima et al. |
| 2006/0244379 A1 | | 11/2006 | Shin |
| 2006/0283746 A1 | | 12/2006 | Sutoh et al. |

(Continued)

FOREIGN PATENT DOCUMENTS

| CN | 1877777 A | 12/2006 |
| CN | 101014668 A | 8/2007 |

(Continued)

OTHER PUBLICATIONS

English translation of JP 2013/233387, Nov. 2013; 9 pages.*

(Continued)

Primary Examiner — Helene Klemanski
(74) Attorney, Agent, or Firm — Westerman, Hattori, Daniels & Adrian, LLP

(57) ABSTRACT

An object of the present invention is to provide: a plasma treatment detection indicator comprising a color-changing layer that exhibits improved heat resistance so that the layer does not change color even when overheated at up to about 170° C. as a result of a plasma-generating gas not being supplied or being insufficient due to a defect in a plasma treatment device; and an ink composition for detecting plasma treatment, the composition being for forming the color-changing layer. The ink composition for detecting plasma treatment includes a colorant and a binder resin containing a phenol resin, and the plasma treatment detection indicator uses the ink composition.

15 Claims, No Drawings

(56) References Cited

U.S. PATENT DOCUMENTS

| | | | |
|---|---|---|---|
| 2008/0090726 A1 | 4/2008 | Eskra et al. | |
| 2008/0267811 A1 | 10/2008 | Yamaguchi et al. | |
| 2009/0212237 A1 | 8/2009 | Sugiki et al. | |
| 2010/0119410 A1 | 5/2010 | Yamaguchi et al. | |
| 2011/0009535 A1 | 1/2011 | Mikumo et al. | |
| 2011/0065203 A1 | 3/2011 | Studer et al. | |
| 2011/0275159 A1 | 11/2011 | Landgrebe et al. | |
| 2011/0312096 A1 | 12/2011 | Whitman et al. | |
| 2012/0100395 A1 | 4/2012 | Feiler et al. | |
| 2014/0154808 A1 | 6/2014 | Patel | |
| 2015/0050745 A1 | 2/2015 | Karato et al. | |
| 2016/0045631 A1* | 2/2016 | Yamaguchi | A61L 2/14 422/28 |
| 2016/0133444 A1* | 5/2016 | Oshiro | H01J 37/32963 216/60 |
| 2016/0141192 A1* | 5/2016 | Uneyama | C09D 11/50 116/201 |
| 2016/0349222 A1* | 12/2016 | Mori | H01J 37/32935 |
| 2017/0044389 A1 | 2/2017 | Mori | |
| 2017/0101548 A1* | 4/2017 | Mori | A61L 2/14 |
| 2017/0153174 A1 | 6/2017 | Yamakawa et al. | |
| 2017/0261476 A1 | 9/2017 | Hishikawa et al. | |
| 2017/0330777 A1 | 11/2017 | Hishikawa et al. | |

FOREIGN PATENT DOCUMENTS

| | | |
|---|---|---|
| EP | 1312918 A2 | 5/2003 |
| GB | 2 168 082 A | 6/1986 |
| JP | 63-36876 A | 2/1988 |
| JP | 1-295423 A | 11/1989 |
| JP | 4-305492 A | 10/1992 |
| JP | 6-69165 A | 3/1994 |
| JP | 7-26477 A | 1/1995 |
| JP | 11-37988 A | 2/1999 |
| JP | 2000-269191 A | 9/2000 |
| JP | 2001-174449 A | 6/2001 |
| JP | 2001-237097 A | 8/2001 |
| JP | 2001-242249 A | 9/2001 |
| JP | 2002-011081 A | 1/2002 |
| JP | 2002-022534 A | 1/2002 |
| JP | 2002-502953 A | 1/2002 |
| JP | 2002-303618 A | 10/2002 |
| JP | 2002/322315 A | 11/2002 |
| JP | 2002-323451 A | 11/2002 |
| JP | 2003-506156 A | 2/2003 |
| JP | 2003-515744 A | 5/2003 |
| JP | 2003-325646 A | 11/2003 |
| JP | 2004-101488 A | 4/2004 |
| JP | 2004-146738 A | 5/2004 |
| JP | 2004-203984 A | 7/2004 |
| JP | 2004-298479 A | 10/2004 |
| JP | 2005-111154 A | 4/2005 |
| JP | 2005-142287 A | 6/2005 |
| JP | 2005-315828 A | 11/2005 |
| JP | 2005-329019 A | 12/2005 |
| JP | 2006-78463 A | 3/2006 |
| JP | 2006-223351 A | 8/2006 |
| JP | 2007-040785 A | 2/2007 |
| JP | 2008-125760 A | 6/2008 |
| JP | 2009-213609 A | 9/2009 |
| JP | 2010-501655 A | 1/2010 |
| JP | 2011-530085 A | 12/2011 |
| JP | 2012-050664 A | 3/2012 |
| JP | 2012-068811 A | 4/2012 |
| JP | 2012-78202 A | 4/2012 |
| JP | 2013-95764 A | 5/2013 |
| JP | 2013-095764 A | 5/2013 |
| JP | 2013-095765 A | 5/2013 |
| JP | 2013-098196 A | 5/2013 |
| JP | 2013-233387 A | 11/2013 |
| JP | 2014-109523 A | 6/2014 |
| JP | 2016-111063 A | 6/2016 |
| WO | 98/46279 A1 | 10/1998 |
| WO | 98/46994 A1 | 10/1998 |
| WO | 99/39754 A1 | 8/1999 |
| WO | 01/10476 A1 | 2/2001 |
| WO | 01/40792 A1 | 6/2001 |
| WO | 2004/087222 A1 | 10/2004 |
| WO | 2006/109726 A1 | 10/2006 |
| WO | 2008/022952 A1 | 2/2008 |
| WO | 2013/129473 A1 | 9/2013 |
| WO | 2014/038612 A1 | 3/2014 |
| WO | WO 2014/196440 A1 * | 12/2014 |
| WO | WO 2015/025699 A1 * | 2/2015 |
| WO | 2015/170592 A1 | 11/2015 |

OTHER PUBLICATIONS

English translation of JP 2013/095765, May 2013; 14 pages.*
English translation of JP 2002/303618, Oct. 2002; 14 pages.*
English translation of JP 2004/101488, Apr. 2004; 9 pages.*
English translation of WO 2014/038612, Mar. 2014; 10 pages.*
Janus Green B, no date available; https://pubchem.ncbi.nlm.nih.gov/compound/Janus_green_B; 17 pages.*
Bakelite BKUA 2370, Georgia Pacific Chemicals Phenolic Resins, no date available, http://www.brenntag.com/specialties/en/product-industries/industries/material-science/composites-and-advanced-materials/georgia-pacific-phenolic-resins-dispersions-composites.jsp; 3 pages.*
Sylowhite SM 405, Jul. 2009, http://novana.ch/news/8/3/0/sylowhite-sm-405; 1 page.*
Masaaki Nagatsu, Plasma Sterilization, Journal of Plasma and Fusion Research, 2007, vol. 83, No. 7, pp. 601-606.
International Search Report dated Jul. 14, 2015, issued in counterpart International Application No. PCT/JP2015/061545.
International Search Report dated Sep. 2, 2014, issued in Application No. PCT/JP2014/064209; 2 pages.
English translation of the Written Opinion of the International Search Authority dated Nov. 17, 2015 for PCT/JP2015/073769; 4 pages.
International Search Report dated Nov. 17, 2015, issued in International Application No. PCT/JP2015/073769; 1 page.
Non-Final Office Action dated Jun. 28, 2017; issued in U.S. Appl. No. 14/895,835; 19 pages.
Non-Final Office Action dated Jun. 30, 2017; issued in U.S Appl. No. 15/316,980; 20 pages.
Final Office Action dated Nov. 17, 2017, issued in U.S. Appl. No. 14/895,835. (18 pages).
International Search Report dated Apr. 14, 2015, issued in counterpart International Application No. PCT/JP2015/053742 (1 page).
International Search Report dated Feb. 9, 2016, issued in counterpart Application No. PCT/JP2015/082841 (2 pages).
International Search Report dated Sep. 16, 2014, issued in counterpart Application No. PCT/JP2014/070419 (2 pages).
Office Action dated Mar. 14, 2017, issued in Chinese Application No. 201480033301.2, with partial English translation (11 pages).
Office Action dated Jun. 9, 2010, issued in counterpart Japanese Application No. 2005-064179 (2 pages).
International Search Report dated May 17, 2005, issued in Application No. PCT/JP2005/006138 (1 page).
Non-Final Office Action dated Mar. 4, 2009, issued in U.S. Appl. No. 10/594,587 (9 pages).
Final Office Action dated Nov. 27, 2009, issued in U.S. Appl. No. 10/594,587 (11 pages).
Non-Final OA dated Jun. 11, 2010, issued in U.S. Appl. No. 10/594,587 (6 pages).
Final Office Action dated Dec. 23, 2010, issued in U.S. Appl. No. 10/594,587 (5 pages).
Notice of Allowance dated Apr. 1, 2011, issued in U.S. Appl. No. 10/594,587 (7 pages).
Non-Final Office Action dated Dec. 19, 2017, issued in U.S. Appl. No. 15/309,510 (16 pages).
Non-Final Office Action dated Jan. 31, 2018, issued in U.S. Appl. No. 15/529,382 (25 Pages).
Non-Final Office Action dated Nov. 20, 2017, issued in U.S. Appl. No. 14/897,461 (27 pages).

(56) References Cited

OTHER PUBLICATIONS

Notice of Allowance dated Nov. 22, 2017, issued in U.S. Appl. No. 15/316,980. (15 pages).
Office Action dated Mar. 20, 2018, issued in counterpart Japanese Application No. 2014-087638, with English translation (9 pages).
Notice of Allowance dated May 1, 2018, issued in U.S. Appl. No. 14/897,461 (27 pages).
Notice of Allowance dated Apr. 27, 2018, issued in U.S. Appl. No. 15/309,510 (24 pages).
International Search Report dated Mar. 1, 2016, issued in counterpart International Application No. PCT/JP2015/082818 (2 pages).
Office Action dated Sep. 28, 2010, issued in counterpart Japanese Application No. 2005-064179, with English translation (5 pages).
Office Action dated Mar. 26, 2013, issued in counterpart Japanese Application No. 2010-263654, with English translation (5 pages).
Notice of Allowance dated May 17, 2018, issued in U.S. Appl. No. 15/117,601 (28 pages).
International Search Report dated Jul. 14, 2015 issued in International Application No. PCT/JP2015/062244 (2 pages).
Notice of Allowance dated Mar. 22, 2018, issued in U.S. Appl. No. 15/316,980 (18 pages).
Non-Final Office Action dated May 17, 2018, issued in U.S. Appl. No. 15/117,601 (28 pages).
Final Office Action dated May 25, 2018, issued in U.S. Appl. No. 15/529,382 (37 pages).
Notice of Allowance dated Jun. 13, 2018, issued in U.S. Appl. No. 15/316,980 (19 pages).
Notice of Allowance dated Aug. 15, 2018, issued in U.S. Appl. No. 15/529,382 (16 pages).
Kitaoka, Kyozo, "Guide for Coatings to Synthetic Resin", May 25, 1974, First Edition, pp. 212-213, with English translation; Cited in Japanese Office Action dated Aug. 21, 2018.
"Toryo Genryo Binran [Paint Material Handbook]", Japan Paint Manufacturers Association, May 31, 1999, 7th Edition, pp. 77-79, with English translation; Cited in Japanese Office Action dated Aug. 21, 2018.
Office Action dated Aug. 21, 2018, issued in Japanese Application No. 2014-087638, with English translation (7 pages).
Notice of Allowance dated Sep. 6, 2018, issued in U.S. Appl. No. 15/309,510 (22 pages).
Office Action dated Aug. 28, 2018, issued in counterpart to Japanese Application No. 2015-532792, with English translation (6 pages).
Office Action dated Sep. 5, 2018, issued in counterpart Chinese Application No. 201580020478.3, with English translation (12 pages).
Office Action dated Oct. 9, 2018, issued in counterpart Japanese Application No. 2015-562838, with English translation (5 pages).
Office Action dated Oct. 9, 2018, issued in counterpart Japanese Application No. 2014-244414, with English translation (7 pages).
Final Office Action dated Sep. 20, 2018, issued in U.S. Appl. No. 15/177,601 (21 pages).
Final Office Action dated Oct. 29, 2018, issued in U.S. Appl. No. 15/117,601 (15 pages).
Final Office Action dated Sep. 20, 2018, issued in U.S. Appl. No. 15/117,601 (21 pages).
Office Action dated Dec. 4, 2018, issued in counterpart Japanese Application No. 2015-095244, with English translation (5 pages).

* cited by examiner

INK COMPOSITION FOR DETECTING PLASMA TREATMENT AND INDICATOR FOR DETECTING PLASMA TREATMENT

TECHNICAL FIELD

The present invention relates to an ink composition for detecting plasma treatment and to a plasma treatment detection indicator using the composition. The plasma treatment as referred to herein means a plasma treatment using a plasma generated by applying AC voltage, pulse voltage, high-frequency waves, microwaves, etc., using a gas for generating plasma. The plasma treatment includes both reduced-pressure plasma and atmospheric-pressure plasma.

BACKGROUND ART

Various types of equipment, instruments, etc., used in hospitals, laboratories, and the like are sterilized for disinfection and killing bacteria and fungi. Plasma treatment is known as a sterilization treatment (see, for example, "3.3.1 Sterilization Experiment Using Low-Pressure Discharge Plasma" in NPL 1).

Plasma treatment is used not only for sterilization treatment but also for plasma dry-etching and plasma cleaning of the surface of articles to be treated, such as electronic parts, in the production of semiconductor devices.

Plasma dry-etching typically comprises applying high-frequency power to electrodes placed in a reaction chamber that is a vacuum vessel, plasmarizing a gas for generating plasma introduced in the reaction chamber, and etching a semiconductor wafer with high precision. Plasma cleaning removes metal oxides, organic substances, burrs, etc., deposited on or adhering to the surface of articles to be treated, such as electronic parts, to improve bonding or wettability of solder, thus enhancing bonding strength and improving adhesion to a sealing resin and wettability.

A method using a plasma treatment detection indicator comprising a color-changing layer that changes color in a plasma treatment atmosphere is known as a method for detecting the completion of these plasma treatments.

For example, PTL 1 discloses an ink composition for detecting plasma treatment comprising 1) at least one of anthraquinone colorants, azo colorants, and phthalocyanine colorants, and 2) at least one of binder resins, cationic surfactants, and extenders, wherein a plasma-generating gas used in the plasma treatment contains at least one of oxygen and nitrogen, and PTL 1 also discloses a plasma treatment detection indicator comprising a color-changing layer formed from the ink composition formed on a base material.

PTL 2 discloses an ink composition for detecting inert gas plasma treatment, comprising (1) at least one of anthraquinone colorants, azo colorants, and methine colorants and (2) at least one of binder resins, cationic surfactants, and extenders, the inert gas containing at least one selected from the group consisting of helium, neon, argon, krypton, and xenon, and PTL 2 also discloses a plasma treatment detection indicator comprising a color-changing layer formed from the ink composition formed on a base material.

These plasma treatment detection indicators are useful because they enable one to determine whether plasma treatment has been completed from the color change of the color-changing layer.

However, when a plasma-generating gas is not supplied or insufficient due to some defect in a plasma treatment device, overheating at up to about 170° C. caused unintentionally by application of AC voltage, pulse voltage, high-frequency waves, microwaves, etc., may change the color of the color-changing layer of these plasma treatment detection indicators. When this occurs, the completion of plasma treatment cannot be accurately determined. Thus, there is room for improvement in heat resistance of the color-changing layer so that overheating at up to about 170° C. as a result of a plasma-generating gas not being supplied or being insufficient does not change the color of the color-changing layer.

Thus, there is a demand for the development of a plasma treatment detection indicator comprising a color-changing layer that exhibits improved heat resistance so that the layer does not change color even when overheated at up to about 170° C. as a result of a plasma-generating gas not being supplied or being insufficient due to a defect in a plasma treatment device, and also an ink composition for detecting plasma treatment for forming the color-changing layer.

CITATION LIST

Patent Literature

PTL 1: JP2013-98196A
PTL 2: JP2013-95764A

Non-Patent Literature

NPL 1: Journal of Plasma and Fusion Research, Vol. 83, No. 7, July 2007

SUMMARY OF INVENTION

Technical Problem

An object of the present invention is to provide a plasma treatment detection indicator comprising a color-changing layer that exhibits improved heat resistance so that the layer does not change color even when overheated at up to about 170° C. as a result of a plasma-generating gas not being supplied or being insufficient due to a defect in a plasma treatment device, and an ink composition for detecting plasma treatment for forming the color-changing layer.

Solution to Problem

The present inventor conducted extensive research to achieve the above object. The inventor found that the object can be achieved by using an ink composition of a specific formulation, and accomplished the present invention.

Specifically, the present invention relates to the following ink compositions for detecting plasma treatment and plasma treatment detection indicators.

1. An ink composition for detecting plasma treatment comprising a colorant and a binder resin, the binder resin containing a phenolic resin.
2. The ink composition according to Item 1, wherein the phenolic resin is at least one member selected from the group consisting of alkyl phenolic resins, terpene phenolic resins, and rosin-modified phenolic resins.
3. The ink composition according to Item 1 or 2, wherein the colorant is at least one member selected from the group consisting of anthraquinone colorants, methine colorants, azo colorants, phthalocyanine colorants, triphenylmethane colorants, and xanthene colorants.
4. The ink composition according to any one of Items 1 to 3, comprising at least one member of nonionic surfactants or cationic surfactants.

5. The ink composition according to any one of Items 1 to 4, comprising an extender.

6. The ink composition according to Item 5, wherein the extender is all or partially silica.

7. The ink composition according to any one of Items 1 to 6, comprising at least one colorant component that does not change color in a plasma treatment atmosphere.

8. A plasma treatment detection indicator comprising a color-changing layer formed from the ink composition according to any one of Items 1 to 7.

9. The indicator according to Item 8, comprising a non-color-changing layer that does not change color in a plasma treatment atmosphere.

10. A plasma treatment package comprising a gas-permeable package and the indicator according to Item 8 or 9 on the inner surface of the gas-permeable package.

11. The package according to Item 10, having a transparent window in a part of the package so as to enable the indicator to be checked from the outside.

12. A plasma treatment method comprising placing one or more articles to be treated in the package according to Item 10 or 11, sealing the package containing the one or more articles to be treated, and placing the package in a plasma treatment atmosphere.

13. The treatment method according to Item 12, wherein the package is placed in a plasma treatment atmosphere until the color-changing layer of the indicator changes color.

The ink compositions for detecting plasma treatment and the plasma treatment detection indicators according to the present invention are described below in detail.

1. Ink Composition for Detecting Plasma Treatment

The ink composition for detecting plasma treatment according to the present invention (hereinafter, may be simply referred to as "ink composition") comprises a colorant and a binder resin, and the binder resin contains a phenolic resin.

Because of the phenolic resin contained in the binder resin in the ink composition for detecting plasma treatment having the feature described above according to the present invention, the color-changing layer formed from the ink composition exhibits higher heat resistance than conventional products. Thus, the color-changing layer does not change color even when overheated at up to about 170° C. as a result of a plasma-generating gas not being supplied or being insufficient due to a defect in a plasma treatment device, and changes color in an appropriate plasma treatment atmosphere. Thus, the plasma treatment detection indicator comprising the color-changing layer enables one to accurately determine whether plasma treatment has been completed.

The following describes each component of the ink composition.

Coloring Agent (Colorant)

A coloring agent (colorant) for detecting plasma for use is preferably at least one member selected from the group consisting of anthraquinone colorants, methine colorants, azo colorants, phthalocyanine colorants, triphenylmethane colorants, and xanthene colorants. The colorants (including dyes) are color-changing colorants that change color because of the change in chemical structure in a plasma treatment atmosphere, and can be used singly, or in a combination of two or more.

Anthraquinone colorants may be any colorant that has anthraquinone as a basic skeleton. Known anthraquinone dispersing dyes and the like are also usable. In particular, anthraquinone colorants containing an amino group are preferable. Anthraquinone colorants containing at least one amino group selected from primary amino groups and secondary amino groups are more preferable. In this case, two or more amino groups may be present, and these amino groups may be of the same or different type.

Specific examples include 1,4-diaminoanthraquinone (C.I. Disperse Violet 1), 1-amino-4-hydroxy-2-methylaminoanthraquinone (C.I. Disperse Red 4), 1-amino-4-methylaminoanthraquinone (C.I. Disperse Violet 4), 1,4-diamino-2-methoxyanthraquinone (C.I. Disperse Red 11), 1-amino-2-methylanthraquinone (C.I. Disperse Orange 11), 1-amino-4-hydroxyanthraquinone (C.I. Disperse Red 15), 1,4,5,8-tetraaminoanthraquinone (C.I. Disperse Blue 1), and 1,4-diamino-5-nitroanthraquinone (C.I. Disperse Violet 8) (color index names are in parentheses).

Other usable colorants include those known as C.I. Solvent Blue 14, C.I. Solvent Blue 35, C.I. Solvent Blue 63, C.I. Solvent Violet 13, C.I. Solvent Violet 14, C.I. Solvent Red 52, C.I. Solvent Red 114, C.I. Vat Blue 21, C.I. Vat Blue 30, C.I. Vat Violet 15, C.I. Vat Violet 17, C.I. Vat Red 19, C.I. Vat Red 28, C.I. Acid Blue 23, C.I. Acid Blue 80, C.I. Acid Violet 43, C.I. Acid Violet 48, C.I. Acid Red 81, C.I. Acid Red 83, C.I. Reactive Blue 4, C.I. Reactive Blue 19, and C.I. Disperse Blue 7.

These anthraquinone colorants can be used singly, or in a combination of two or more. Of these anthraquinone colorants, C.I. Disperse Blue 7, C.I. Disperse Violet 1, and the like are preferable. In the present invention, detection sensitivity can be controlled by changing the types (molecular structures etc.) of such anthraquinone colorants used.

The methine colorants may be any colorant that has a methine group. Polymethine colorants, cyanine colorants, and the like are thus also included within the scope of methine colorants in the present invention. These colorants can be appropriately selected from known or commercially available methine colorants. Specific examples include C.I. Basic Red 12, C.I. Basic Red 13, C.I. Basic Red 14, C.I. Basic Red 15, C.I. Basic Red 27, C.I. Basic Red 35, C.I. Basic Red 36, C.I. Basic Red 37, C.I. Basic Red 45, C.I. Basic Red 48, C.I. Basic Yellow 11, C.I. Basic Yellow 12, C.I. Basic Yellow 13, C.I. Basic Yellow 14, C.I. Basic Yellow 21, C.I. Basic Yellow 22, C.I. Basic Yellow 23, C.I. Basic Yellow 24, C.I. Basic Violet 7, C.I. Basic Violet 15, C.I. Basic Violet 16, C.I. Basic Violet 20, C.I. Basic Violet 21, C.I. Basic Violet 39, C.I. Basic Blue 62, and C.I. Basic Blue 63. These can be used singly, or in a combination of two or more.

The azo colorants may be any colorant that has azo-N=N— as a chromophore. Examples of such colorants include monoazo colorants, polyazo colorants, metal complex salt azo colorants, stilbene azo colorants, and thiazole azo colorants. As indicated by color index names, specific examples of such colorants include C.I. Solvent Red 1, C.I. Solvent Red 3, C.I. Solvent Red 23, C.I. Disperse Red 13, C.I. Disperse Red 52, C.I. Disperse Violet 24, C.I. Disperse Blue 44, C.I. Disperse Red 58, C.I. Disperse Red 88, C.I. Disperse Yellow 23, C.I. Disperse Orange 1, C.I. Disperse Orange 5, and C.I. Disperse Red 167:1. These colorants may be used singly, or in a combination of two or more.

The phthalocyanine colorants may be any colorant that has a phthalocyanine structure. Examples of such colorants include blue copper phthalocyanine, greenish blue metal-free phthalocyanine, green highly chlorinated phthalocyanine, and yellowish green poorly chlorinated phthalocyanine (brominated chlorinated copper phthalocyanine). Specific examples of such colorants include C.I. Pigment Green 7, C.I. Pigment Blue 15, C.I. Pigment Blue 15:3, C.I. Pigment Blue 15:4, C.I. Pigment Blue 15:6, C.I. Pigment Blue 16, C.I. Pigment Green 36, C.I. Direct Blue 86, C.I. Basic Blue 140, and C.I. Solvent Blue 70. These phthalocyanine colorants can be used singly, or in a combination of two or more.

In addition to the typical phthalocyanine colorants listed above, other phthalocyanine colorants are also usable. Examples of such colorants include compounds that have as central metal(s) at least one metal selected from the group consisting of zinc, iron, cobalt, nickel, lead, tin, manganese, magnesium, silicon, titanium, vanadium, aluminum, iridium, platinum, and ruthenium, with the central metal(s) being coordinated with phthalocyanine; such compounds in which the central metal(s) are bonded to oxygen or chlorine and are coordinated with phthalocyanine; and the like.

The triphenylmethane colorants may be any colorant that has a triphenylmethane structure. Examples of triphenylmethane colorants include C.I. Acid Blue 90, C.I. Acid Green 16, C.I. Acid Violet 49, C.I. Basic Red 9, C.I. Basic Blue 7, C.I. Acid Violet 1, C.I. Direct Blue 41, C.I. Mordant Blue 1, and C.I. Mordant Violet 1. These triphenylmethane colorants can be used singly, or in a combination of two or more.

The xanthene colorants may be any colorant that has a xanthene structure. Examples of xanthene colorants include C.I. Acid Yellow 74, C.I. Acid Red 52, C.I. Acid Violet 30, C.I. Basic Red 1, C.I. Basic Violet 10, C.I. Mordant Red 27, and C.I. Mordant Violet 25. These xanthene colorants can be used singly, or in a combination of two or more.

The content of the coloring agent can be appropriately determined according to the type of coloring agent, the desired hue, etc. The ink composition typically preferably contains a coloring agent in an amount of about 0.05 to 5 wt. %, particularly preferably about 0.1 to 1 wt. %.

In the present invention, colorants and pigments other than the coloring agents listed above may also be present. In particular, a coloring agent that does not change in its chemical structure in a plasma treatment atmosphere ("non-color-changing colorant" in this specification) may be added. This can enhance the visual recognition effect due to color tone changes from one color to another. The non-color-changing colorant for use may be a known ink (normal color ink). When such a non-color-changing colorant is used, the content of the non-color-changing colorant can be appropriately determined according to the type of non-color-changing colorant used etc. The scope of the non-color-changing colorant encompasses pigments whose chemical structure does not change in a plasma treatment atmosphere.

Binder Resin

The ink composition according to the present invention comprises a phenolic resin as a binder resin. The phenolic resin has an action to improve the heat resistance of the ink composition and the color-changing layer formed from the ink composition.

The phenolic resin may be any resin that has a phenol structure. For example, at least one member selected from the group consisting of alkyl phenolic resins, terpene phenolic resins, and rosin-modified phenolic resins can be suitably used. Such phenolic resins can be used singly, or in a combination of two or more.

The content of the phenolic resin in the ink composition can be appropriately determined according to the types of phenolic resin and coloring agent used, etc. The amount of the phenolic resin in the ink composition is typically preferably about 0.5 to 50 wt. %, more preferably about 1 to 35 wt. %, and most preferably about 1 to 10 wt. %. When the content of the phenolic resin is less than 0.5 wt. %, the improvement of heat resistance may not be sufficiently achieved. A phenolic resin content exceeding 50 wt. % may make the printed layer brittle during the formation of the color-changing layer by printing using the ink composition, thus making it difficult to handle the layer.

The ink composition of the present invention not only contains the phenolic resin as an essential component, but may also optionally contain other binder resin(s) in combination (hereinafter, other binder resin(s) are referred to as "binder resin(s) usable in combination" to distinguish them from the phenolic resin).

The binder resin(s) usable in combination include a wide range of known resins used in, for example, ink compositions for writing, printing, etc. Examples of binder resin(s) usable in combination include maleic resins, ketone resins, polyvinyl butyral resins, cellulose resins, acrylic resins, styrene maleic resins, styrene acrylic acid resins, polyester resins, polyamide resins, polyacrylonitrile resins, polyimide resins, polyvinyl pyrrolidone resins, polyacrylamide resins, polyvinyl imidazole resins, polyethylene imine resins, and amino resins.

In the present invention, cellulose resins can be suitably used as the binder resin(s) usable in combination. The use of a cellulose resin can impart excellent fixing properties, even when the ink composition contains an extender (e.g., silica). Thus, when a color-changing layer formed from the ink composition is formed on a base material, the layer is efficiently prevented from falling or detaching from the base material. Multiple cracks effectively made on the surface of the coating film of the ink composition can also help enhance the sensitivity of the indicator.

In the present invention, the binder resin(s) usable in combination may be nitrogen-containing polymers, as well as the resins listed above. The nitrogen-containing polymers function not only as a binder, but also as a sensitivity enhancer. Specifically, the use of such a sensitivity enhancer can enhance the accuracy (sensitivity) of plasma treatment detection. Because this ensures color change even in a package for detecting plasma treatment, the indicator can be used very advantageously for the package.

Examples of suitably usable nitrogen-containing polymers include synthetic resins, such as polyamide resins, polyimide resins, polyacrylonitrile resins, amino resins, polyacrylamides, polyvinylpyrrolidones, polyvinylimidazoles, and polyethyleneimines. These resins can be used singly, or in a combination of two or more. Of these, polyamide resins are preferably used. The type, molecular weight, etc., of polyamide resins are not particularly limited, and known or commercially available polyamide resins can be used. Of these, a polyamide resin that is a reaction product of a dimer of linoleic acid with a diamine or polyamine (a long-chain linear polymer) is suitable for use. Polyamide resins are thermoplastic resins with a molecular weight of 4000 to 7000. Commercially available products of these resins can also be used.

The content of the binder resin(s) usable in combination can be appropriately determined according to the types of binder resin and coloring agent used, etc. The amount of the binder in the ink composition is typically preferably about 0.5 to 50 wt. %, and more preferably about 1 to 35 wt. %. When the content of the binder resin(s) usable in combination is less than 0.5 wt. %, the fixing properties of the color-changing layer formed from the ink composition may not be sufficiently achieved. When the content of the binder resin(s) usable in combination exceeds 50 wt. %, the ink composition may become overly viscous, making it difficult to handle the composition.

The ink composition of the present invention may optionally contain, in addition to the coloring agent and the binder resin, any additive such as a surfactant (nonionic surfactant and/or cationic surfactant), an oxygen-containing additive, and an extender.

Nonionic Surfactant

The nonionic surfactant functions as a color change accelerator, and the use of the nonionic surfactant in combination with a coloring agent can provide better detection sensitivity.

At least one of the nonionic surfactants represented by formulae (I) to (V) can be used as a nonionic surfactant.

The nonionic surfactants represented by formula (I) below

$$R_1-X-(AO)_n-R_2 \quad (I)$$

(wherein $R_1$ and $R_2$ are each independently hydrogen, or a straight-chain or branched aliphatic hydrocarbon group having 1 to 30 carbon atoms; X is oxygen or an ester bond; AO is a repeating unit derived from an alkylene oxide; and n is an integer of 1 to 200) are alkylene glycol derivatives.

The nonionic surfactants represented by formula (II) below

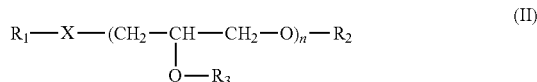

(wherein $R_1$, $R_2$, and $R_3$ are each independently hydrogen, or a straight-chain or branched aliphatic hydrocarbon group having 1 to 30 carbon atoms; X is oxygen or an ester bond; and n is an integer of 1 to 200) are polyglycerin derivatives.

In formula (I), examples of AO (monomer) include ethylene oxide, propylene oxide, 1,2-butylene oxide, 2,3-butylene oxide, tetrahydrofuran, and styrene oxide. The form of polymerization of AO may be a homopolymer, or a block copolymer or a random copolymer of two or more types of AO. In formulae (I) and (II), "having 1 to 30 carbon atoms" refers to preferably having 1 to 22 carbon atoms, and more preferably having 10 to 18 carbon atoms. X is preferably oxygen, and n is preferably an integer of 1 to 100.

Specific examples of nonionic surfactants that can be represented by the above formula (I) or (II) include polyethylene glycols (e.g., the commercially available product PEG2000, produced by Sanyo Chemical Industries, Ltd.), glycerol, and polyethylene glycol-polypropylene glycol copolymers (e.g., the commercially available product Epan 710, produced by Dai-Ichi Kogyo Seiyaku Co., Ltd.).

In the above, polymers wherein at least one of $R_1$ and $R_2$ is replaced with a straight-chain or branched aliphatic hydrocarbon group having 1 to 30 carbon atoms are also preferable.

Specific examples include polyoxyethylene (hereinafter "POE") lauryl ethers (e.g., the commercially available product Emulgen 109P), POE cetyl ethers (e.g., the commercially available product Emulgen 220), POE oleyl ethers (e.g., the commercially available product Emulgen 404), POE stearyl ethers (e.g., the commercially available product Emulgen 306), and POE alkyl ethers (e.g., the commercially available product Emulgen LS-110) (all produced by Kao Corp.); POE tridecyl ethers (e.g., the commercially available product Fine Serve TD-150) and polyethylene glycol monostearates (e.g., the commercially available product Blaunon S-400A) (both produced by Aoki Oil Industrial Co., Ltd.); polyethylene glycol monooleates (e.g., the commercially available product Nonion O-4), tetramethylene glycol derivatives (e.g., the commercially available product polyserine DC-1100), polybutylene glycol derivatives (e.g., the commercially available product Uniol PB-500), and alkylene glycol derivatives (e.g., the commercially available product Unilube 50 MB-5) (all produced by NOF Corporation); and POE(20) octyldodecyl ethers (e.g., the commercially available product Emma Rex OD-20) and POE(25) octyldodecyl ethers (e.g., the commercially available product Emma Rex OD-25) (both produced by Japan Emulsion Co. Ltd.).

The nonionic surfactants represented by formulae (III) and (IV) below

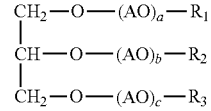

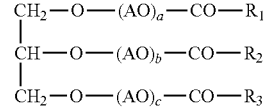

(wherein $R_1$, $R_2$, and $R_3$ are each independently hydrogen or a straight-chain or branched aliphatic hydrocarbon group having 1 to 30 carbon atoms; AO is a repeating unit derived from an alkylene oxide; and the sum of a, b, and c is an integer of 3 to 200) are alkylene glycol glyceryl derivatives.

In both of the above formulae, examples of AO (monomer) include ethylene oxide, propylene oxide, 1,2-butylene oxide, 2,3-butylene oxide, tetrahydrofuran, and styrene oxide. The form of polymerization of AO may be a homopolymer, or a block copolymer or a random copolymer of two or more types of AO. In both of the above formulae, "having 1 to 30 carbon atoms" refers to preferably having 1 to 22 carbon atoms, and more preferably having 10 to 18 carbon atoms; and the sum of a, b, and c is preferably an integer of 3 to 50.

Examples of nonionic surfactants represented by formula (III) include compounds wherein $R_1$ is an isostearic acid residue, $R_2$ and $R_3$ are hydrogen, and AO (monomer) is ethylene oxide. Specific examples include POE glyceryl isostearates (e.g., the commercially available product Uniox GM-30IS, produced by NOF Corporation).

Examples of nonionic surfactants represented by formula (IV) include compounds wherein $R_1$ to $R_3$ are isostearic acid residues, and AO (monomer) is ethylene oxide. Specific examples include POE glyceryl triisostearate (e.g., the commercially available product Uniox GT-30IS, produced by NOF Corporation).

The nonionic surfactants represented by formula (V) below

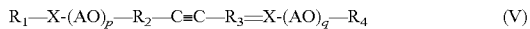
$$R_1-X-(AO)_p-R_2-C\equiv C-R_3=X-(AO)_q-R_4 \quad (V)$$

(wherein $R_1$, $R_2$, $R_3$, and $R_4$ are each independently hydrogen or a straight-chain or branched aliphatic hydrocarbon group having 1 to 30 carbon atoms, X is oxygen or an ester bond, AO is a repeating unit derived from alkylene oxide, and the sum of p and q is an integer of 0 to 20) are acetylene glycol derivatives.

In formula (V), examples of AO (monomer) include ethylene oxide, propylene oxide, 1,2-butylene oxide, 2,3-butylene oxide, tetrahydrofuran, and styrene oxide. The form of polymerization of AO may be a homopolymer, or a block copolymer or a random copolymer of two or more types of AO. In formulae (I) and (II), "having 1 to 30 carbon atoms" refers to preferably having 1 to 22 carbon atoms, X is preferably oxygen, and the sum of p and q is preferably an integer of 0 to 10.

Examples of nonionic surfactants represented by formula (V) include compounds wherein $R_1$ and $R_4$ are hydrogen, $R_2$ and $R_3$ are >C(CH$_3$) (i-C$_4$H$_9$), X is oxygen, and the sum of p and q is 0. Specific examples include 2,4,7,9-tetramethyl-5-decyn-4,7-diol (e.g., the commercially available product Surfynol 104H, produced by Air Products Japan, Inc.).

The nonionic surfactants represented by formulae (I) to (V) can be used singly, or in a combination of two or more.

The content of the nonionic surfactant can be appropriately determined according to the types of nonionic surfactant and coloring agent used, etc. In consideration of its preservability in the composition and color-change-accelerating effect, the content of the nonionic surfactant in the ink composition is typically preferably about 0.2 to 10 wt. %, and particularly preferably 0.5 to 5 wt. %.

Cationic Surfactant

Although there is no particular limitation, it is desirable to use, in particular, at least one of tetraalkylammonium salts, isoquinolinium salts, imidazolinium salts, and pyridinium salts as a cationic surfactant. Commercially available products of these salts can also be used. The use of a cationic surfactant in combination with the coloring agent can provide greater detection sensitivity. These cationic surfactants can be used singly, or in a combination of two or more.

Of tetraalkylammonium salts, alkyltrimethylammonium salts, dialkyldimethylammonium salts, and the like are preferable. Specific examples include cocoalkyltrimethylammonium chloride, tallowalkyltrimethylammonium chloride, behenyltrimethylammonium chloride, myristyltrimethylammonium chloride, tetramethylammonium chloride, tetrabutylammonium chloride, tetrapropylammnonium chloride, tetramethylanmonium bromide, tetrabutylammonium bromide, tetrapropylammonium bromide, trimethyl-2-hydroxyethyl ammonium chloride, cetyltrimethylammonium chloride, lauryltrimethylammonium chloride, stearyltrimethylammonium chloride, dioctyldimethylammnonium chloride, distearyldimethylammonium chloride, and alkylbenzyldimethylammonium chloride. In particular, behenyltrimethylammnonium chloride, lauryltrimethylammonium chloride, and the like are preferable.

Examples of isoquinolinium salts include laurylisoquinolinium bromide, cetylisoquinolinium bromide, cetylisoquinolinium chloride, and laurylisoquinolinium chloride. Of these, laurylisoquinolinium bromide is particularly preferable.

Examples of imidazolinium salts include 1-hydroxyethyl-2-oleylimidazolinium chloride, and 2-chloro-1,3-dimethylimidazolinium chloride. Of these, 2-chloro-1,3-dimethylimidazolinium chloride is particularly preferable.

Examples of pyridinium salts include pyridinium chloride, 1-ethylpyridinium bromide, hexadecylpyridinium chloride, cetylpyridinium chloride, 1-butylpyridinium chloride, N-n-butylpyridinium chloride, hexadecylpyridinium bromide, N-hexadecylpyridinium bromide, 1-dodecylpyridinium chloride, 3-methylhexylpyridinium chloride, 4-methylhexylpyridinium chloride, 3-methyloctylpyridinium chloride, 2-chloro-1-methylpyridinium iodide, 3,4-dimethylbutylpyridinium chloride, pyridinium-n-hexadecyl chloride-hydrate, N-(cyanomethyl)pyridinium chloride, N-acetonylpyridinium bromide, 1-(aminoformylmethyl) pyridinium chloride, 2-amidinopyridinium chloride, 2-aminopyridinium chloride, N-aminopyridinium iodide, 1-aminopyridinium iodide, 1-acetonylpyridinium chloride, and N-acetonylpyridinium bromide. Of these, hexadecylpyridinium chloride is particularly preferable. The content of the cationic surfactant can be appropriately determined according to the types of cationic surfactant and coloring agent used, etc., and the content of the cationic surfactant in the ink composition is typically preferably about 0.2 to 10 wt. %, and particularly preferably 0.5 to 5 wt. %.

Extender

Any extender can be used without particular limitation, and examples of extenders include bentonite, activated clay, aluminum oxide, silica, silica gel, and like inorganic materials. Materials known as extender pigments can also be used. Of these, at least one member selected from the group consisting of silica, silica gel, and alumina is preferable, and silica is particularly preferable. When silica or the like is used, multiple cracks can be effectively produced particularly on the surface of the color-changing layer. As a result, the detection sensitivity of the indicator can be further enhanced. The extenders can be used singly, or in a combination of two or more.

The content of the extender can be appropriately determined according to the types of extender and coloring agent used, etc. The content of the extender in the ink composition is typically preferably about 1 to 30 wt. %, and particularly preferably 2 to 20 wt. %.

Other Additives

The ink composition may optionally and appropriately contain components used in known inks, such as solvents, leveling agents, antifoaming agents, UV absorbers, and surface conditioners.

Solvents that can be used in the present invention may be any solvent that is typically used in ink compositions for printing, writing, etc. Usable solvents are various solvents such as alcohol-based, polyhydric alcohol-based, ester-based, ether-based, ketone-based, hydrocarbon-based, and glycol ether-based solvents. The solvent to be used can be appropriately selected according to the solubility of the colorant and binder resin used, etc. The solvents can be used singly, or in a combination of two or more.

The content of the solvent can be appropriately determined according to the types of solvent and coloring agent used, etc., and the content of the solvent in the ink composition is typically preferably about 40 to 95 wt. %, and particularly preferably 60 to 90 wt. %.

The components of the ink composition of the present invention can be added at one time or sequentially, and mixed uniformly using a known stirrer, such as a homogenizer or a dissolver. For example, the coloring agent and at least one of binder resins, cationic surfactants, or extenders (other additives as required) may be sequentially added to a solvent, and the resultant mixture may be mixed and stirred using a stirrer.

The components of the ink composition of the present invention can be added at one time or sequentially, and mixed uniformly using a known stirrer, such as a homogenizer or a dissolver. For example, the coloring agent and at least one of binder resins, cationic surfactants, or extenders (other additives as required) may be sequentially added to a solvent, and the resultant mixture may be mixed and stirred using a stirrer.

2. Plasma Treatment Detection Indicator

The indicator according to the present invention comprises a color-changing layer formed from the ink composition of the present invention. The color-changing layer can typically be formed by applying or printing the ink composition of the present invention on a base material. Any base material can be used as the base material insofar as the color-changing layer can be formed on the base material.

Examples of base materials include metals or alloys, ceramics, glass, concrete, plastics (polyethylene terephthalate (PET), polypropylene, nylon, polystyrene, polysulfone, polycarbonate, polyimide, etc.), fibers (non-woven fabric, woven fabric, other fibrous sheets), and composite materials thereof. Synthetic resin fiber paper (synthetic paper), such as polypropylene synthetic paper and polyethylene synthetic paper, can also be suitably used.

The color-changing layer of the present invention includes layers that change color to other colors, and also includes layers that fade in color or become decolorized.

The color-changing layer can be formed using the ink composition of the present invention according to known printing methods, such as silk-screen printing, gravure printing, offset printing, relief printing, and flexographic printing. The color-changing layer can also be formed by various methods other than printing methods. For example, the color-changing layer can be formed by immersing a base material into an ink composition. This method is particularly suitable for materials into which ink permeates, such as nonwoven fabrics.

The color-changing layer preferably has multiple cracks on the surface. Specifically, the color-changing layer is preferably porous with open pores formed on the surface of the layer. This structure can further enhance the sensitivity in plasma treatment detection. With this structure, even a color-changing layer placed inside the plasma treatment detection package can exhibit a desired color change effect. Cracks can be effectively formed by using a cellulose resin as a binder resin for the ink composition of the present invention. Specifically, the use of a cellulose resin enables the formation of cracks as described above, while maintaining good fixing properties.

In the present invention, a non-color-changing layer whose color does not change in a plasma treatment atmosphere may be further formed on the base material and/or on the color-changing layer. The non-color-changing layer can typically be formed by using a commercially available normal color ink. For example, water-based inks, oil-based inks, solvent-free inks, and the like can be used. The ink for use in the formation of the non-color-changing layer may contain components used in known inks, such as resin binders, extenders, and solvents.

The non-color-changing layer may be formed in the same manner as in the formation of the color-changing layer. For example, the non-color-changing layer can be formed by using a normal color ink according to a known printing method, such as silk-screen printing, gravure printing, offset printing, relief printing, or flexographic printing. The order of printing the color-changing layer and the non-color-changing layer is not particularly limited, and may be appropriately selected according to the design to be printed etc.

The indicator of the present invention may comprise one color-changing layer and one non-color-changing layer, or two or more color-changing layers and two or more non-color-changing layers. Color-changing layers may be laminated together, or non-color-changing layers may be laminated together. In this case, the compositions of the color-changing layers may be the same or different. Likewise, the compositions of the non-color-changing layers may be the same or different.

Further, the color-changing layer and the non-color-changing layer may be formed partially or entirely on the base material or on the layers. In this case, in particular, in order for the color-changing layer to reliably change color, it is sufficient that color-changing layer(s) and non-color-changing layer(s) be formed in such a manner that at least one color-changing layer is partially or entirely exposed to a plasma treatment atmosphere.

In the present invention, the color-changing layer and non-color-changing layer may be freely combined insofar as completion of the plasma treatment can be confirmed. For example, the color-changing layer and non-color-changing layer can be formed in such a manner that the color difference between them can be recognized only after the color of the color-changing layer changes, or in such a manner that the color difference between them disappears only after the color of the color-changing layer changes. In the present invention, it is particularly preferable to form the color-changing layer and non-color-changing layer in such a manner that the color difference between them can be recognized only after the color of the color-changing layer changes.

To enable the color difference to be recognized, for example, the color-changing layer and non-color-changing layer may be formed in such a manner that at least one of characters, patterns, or symbols appear only after the color of the color-changing layer changes. In the present invention, characters, patterns, and symbols include any information that indicates color change. Such characters and the like may be appropriately designed according to the intended use etc.

The color of the non-color-changing layer and the color of the color-changing layer before color change may be different from each other. For example, the color-changing layer and the non-color-changing layer may have substantially the same color, and the color difference (contrast) between the color-changing layer and the non-color-changing layer may be made recognizable only after color change occurs.

According to the indicator of the present invention, the color-changing layer and the non-color-changing layer can be formed in such a manner that the color-changing layer and the non-color-changing layer do not overlap. This can save the amount of ink used.

In the present invention, another color-changing layer or non-color-changing layer may be further formed on either the color-changing layer or the non-color-changing layer, or both. For example, when a color-changing layer having a different design is formed on a layer comprising a color-changing layer and a non-color-changing layer formed in such a manner that the color-changing layer and the non-color-changing layer do not overlap (referred to as "a color changing/non-color-changing layer"), the boundary between the color-changing layer and the non-color-changing layer in the color changing/non-color-changing layer cannot be substantially recognized. Thus, better design can be attained.

The indicator of the present invention is applicable to any plasma treatment using a plasma-generating gas. Thus, the indicator can be used for both reduced-pressure plasma treatment and atmospheric-pressure plasma treatment.

Reduced-pressure plasma treatments may be used, for example, in film production, ashing, cleaning, surface modification, etc., of flat-panel displays (e.g., liquid crystal displays); film production, ashing, cleaning, surface modification, etc., in semiconductor manufacturing processes; cleaning, surface modification, etc., of mounting substrates or printed-circuit substrates; sterilization, etc., of medical instruments; and cleaning, surface modification, etc., of mounted components.

Atmospheric-pressure plasma treatments can be used, for example, in cleaning, surface modification, etc., of flat-panel displays (e.g., liquid crystal displays); cleaning, surface modification, etc., of mounting substrates or printed-circuit substrates; surface modification of automobiles, aircraft components, etc.; and disinfection, sterilization, medical treatment, etc., in the medical field (dentistry or surgery).

The gas for generating reduced-pressure plasma may be any gas that can generate plasma by applying AC voltage, pulse voltage, high-frequency waves, microwaves, etc., under reduced pressure. Examples of such gases include oxygen, nitrogen, hydrogen, chlorine, hydrogen peroxide, helium, argon, silane, ammonia, sulfur bromide, water vapor, nitrous oxide, tetraethoxysilane, carbon tetrafluoride, trifluoromethane, carbon tetrachloride, silicon tetrachloride, sulfur hexafluoride, titanium tetrachloride, dichlorosilane, trimethylgallium, trimethylindium, and trimethylaluminum. These gases for generating reduced-pressure plasma can be used singly, or in a combination of two or more.

The gas for generating atmospheric-pressure plasma may be any gas that can generate plasma by applying AC voltage, pulse voltage, high-frequency waves, microwaves, etc., under atmospheric pressure. Examples of such gases include oxygen, nitrogen, hydrogen, argon, helium, and air. These gases for generating atmospheric-pressure plasma can be used singly, or in a combination of two or more.

When the indicator of the present invention is used, for example, the indicator of the present invention may be placed in a plasma treatment device that uses a plasma-generating gas (specifically, a device for plasma treatment that generates plasma by application of AC voltage, pulse voltage, high-frequency waves, microwaves, etc., in an atmosphere containing a plasma-generating gas to perform plasma treatment) or placed on or near the article(s) to be treated that are accommodated in the device, and may be exposed to a plasma treatment atmosphere. In this case, it can be detected from the color change of the indicator placed in the device that a predetermined plasma treatment has been performed.

The indicator of the present invention can be used in the form of an indicator card as is. If the color-changing layer is in the form of a known bar code and the bar code has its conditions set so that it can be read by a bar code reader at the stage where a predetermined plasma treatment has been completed (degree of color change), completion of plasma treatment and subsequent plasma-treated article distribution management can be centrally managed with the bar code. The present invention also includes inventions of an indicator, a method for plasma treatment management, and a method for distribution management used for this purpose.

3. Package

The present invention includes a package for plasma treatment comprising a gas-permeable package and the indicator of the present invention placed on the inner surface of the package.

The gas-permeable package is preferably a package that can be subjected to a plasma treatment with article(s) to be treated being contained in the package. Known or commercially available packages that are used as packages (pouches) for plasma treatment can be used. For example, a package formed of polyethylene fiber (polyethylene synthetic paper) can be suitably used. After the article(s) to be treated are placed in this package and the opening is sealed by heat-sealing or the like, the entire package can be treated in the plasma treatment device.

The indicator of the present invention may be placed on the inner surface of the package. The method for disposing the indicator is not particularly limited. In addition to methods using adhesives, heat-sealing, etc., the indicator can also be formed by directly applying or printing the ink composition of the present invention onto the inner surface of the package. When an indicator is formed by such application or printing, the indicator can also be formed at the stage of manufacturing the package.

The package of the present invention preferably has a transparent window in a part of the package so as to allow the indicator to be visually checked from the outside. For example, the package may be formed using a transparent sheet and the polyethylene synthetic paper mentioned above, and the indicator may be placed on the inner surface of the package at such a position as to allow the indicator to be visually checked through the transparent sheet.

When plasma treatment is performed using the package of the present invention, a method including the following steps may be used: a step of placing article(s) to be treated into the package, a step of sealing the package containing the article(s) to be treated, and a step of disposing the package in a plasma treatment atmosphere. More specifically, after the article(s) to be treated are placed in the package, the package is sealed according to a known method, such as heat sealing. Subsequently, the entire package is placed in a plasma treatment atmosphere. For example, the package is placed in a treatment chamber of a known or commercially available plasma treatment device, and subjected to the treatment. After the treatment has been completed, the entire package is removed from the treatment chamber, and the treated article(s) can be kept in the package as is until use. In this plasma treatment, the package is preferably kept in a plasma treatment atmosphere until the color of the color-changing layer of the indicator changes.

Advantageous Effects of Invention

Because of the phenolic resin contained in the binder resin in the ink composition for detecting plasma treatment according to the present invention, the color-changing layer formed from the ink composition exhibits higher heat resistance than conventional products. Thus, the color-changing layer does not change color even when overheated at up to about 170° C. as a result of a plasma-generating gas not being supplied or being insufficient due to a defect in a plasma treatment device and changes color in an appropriate plasma treatment atmosphere. Thus, a plasma treatment detection indicator comprising the color-changing layer enables one to accurately determine whether plasma treatment has been completed.

DESCRIPTION OF EMBODIMENTS

The following shows Examples and Comparative Examples to further clarify the feature of the present invention. However, the present invention is not limited to the embodiments of the Examples.

Examples 1 to 4 and Comparative Examples 1 to 3

Ink compositions were prepared by mixing the components according to the formulations shown in Table 1.

The ink compositions were individually silk-screen-printed on a white Toyobo Crisper K2323 PET film, and dried at room temperature for 30 minutes or more, followed by drying at 80° C. for 20 minutes, thereby obtaining indicators.

Test Example 1

Each indicator was subjected to a heat resistance test and to a color change test. The test methods and evaluation criteria are as follows.

Heat Resistance Test

First, the chromaticity L*a*b* of the color-changing layer of each indicator (before heat treatment) was measured with an NR-11A handheld colorimeter, produced by Nippon Denshoku Industries Co., Ltd.

Next, each indicator was heat-treated by being allowed to stand in a thermostatic bath at 170° C. for 10 minutes. These conditions were intended to simulate a situation in which unintended overheating occurs because a plasma-generating gas is not appropriately supplied in a plasma treatment device due to some defects.

After each indicator was allowed to stand for 10 minutes, the indicator was removed from the device, and the chromaticity L*a*b* of the color-changing layer (after heat treatment) was measured in the same manner as above.

The chromaticity before the heat treatment was defined as $L^*_1$, $a^*_1$, and $b^*1$, whereas the chromaticity after the heat treatment was defined as $L^*_2$, $a^*_2$, and $b^*_2$. The difference in chromaticity (color difference) between the two, which is indicated by $\Delta E^*ab$, was calculated using the following equation.

$$\text{Color difference } \Delta E^*ab=[(L^*_2-L^*_1)^2+(a^*_2-a^*_1)^2+(b^*_2-b^*_1)^2]^{1/2}$$

Table 1 shows the test results.

Color Change Test

First, the chromaticity L*a*b* of the color-changing layer of each indicator (before plasma treatment) was measured with an NR-11A handheld colorimeter, produced by Nippon Denshoku Industries Co., Ltd.

Next, each indicator was placed in a BP-1 high-frequency plasma treatment device (produced by Samco Inc.).

$O_2$ gas and Ar gas were prepared as a plasma-generating gas, and plasma treatment was performed under the following conditions. The chromaticity L*a*b* of each color-changing layer after plasma treatment was measured in the same manner as above.

The chromaticity before the plasma treatment was defined as $L^*_1$, $a^*_1$, and $b^*_1$, whereas the chromaticity after the plasma treatment was defined as $L^*_2$, $a^*_2$, and $b^*_2$. The difference in chromaticity (color difference) between the two, which is indicated by $\Delta E^*ab$, was calculated using the following equation.

$$\text{Color difference } \Delta E^*ab=[(L^*_2-L^*_1)^2+(a^*_2-a^*_1)^2+(b^*_2-b^*_1)^2]^{1/2}$$

Plasma Treatment Conditions
Treatment Conditions Using $O_2$ Gas
  $O_2$ gas: 10 ml/min, CF4 gas: 5 ml/min
  Electric Power: 75 W, Pressure: 100 Pa, Distance Between Electrodes: 50 mm
  Treatment Time: 20 min
Treatment Conditions Using Ar Gas
  Ar gas: 20 ml/min
  Electric Power: 75 W, Pressure: 20 Pa, Distance Between Electrodes: 50 mm
  Treatment Time: 30 min
Analysis As is clear from the results shown in Table 1, the color-changing layers in Examples 1 to 4 exhibited heat resistance of $\Delta E^*ab \leq 5$, and visual examination found no substantial change. The color-changing layers in Comparative Examples 1 to 3 exhibited a larger $\Delta E^*ab$, and color change of the layers owing to the temperature was observed. Regarding the color change, the color change rate of the color-changing layers in the Examples was slower than that of the color-changing layers in the Comparative Examples because of the absence of color change by heat.

Test Example 2

Color Change Test

First, the chromaticity L*a*b* before plasma treatment of the color-changing layer of the indicator in Example 1, which was prepared using the ink composition of Example 1, was measured with an NR-11A handheld colorimeter, produced by Nippon Denshoku Industries Co., Ltd.

Next, the indicator of Example 1 was subjected to various plasma treatments described below, and the chromaticity L*a*b* of the color-changing layer after plasma treatment was measured in the same manner as above.

The chromaticity before the plasma treatment was defined as $L^*_1$, $a^*_1$, and $b^*_1$, whereas the chromaticity after the plasma treatment was defined as $L^*_2$, $a^*_2$, and $b^*_2$. The difference in chromaticity (color difference) between the two, which is indicated by $\Delta E^*ab$, was calculated using the following equation.

$$\text{Color difference } \Delta E^*ab=[(L^*_2-L^*_1)^2+(a^*_2-a^*_1)^2+(b^*_2-b^*_1)^2]^{1/2}$$

In each of the plasma treatments, the color change (color difference) $\Delta E^*ab$ between before and after the treatment was confirmed to be 5 or more. Specifically, the results demonstrate that the completion of the plasma treatments can be confirmed.

Plasma Treatment Conditions
Plasma Treatment (1): Water Vapor/Hydrogen Peroxide Plasma
  Device: BP-1 High-frequency plasma treatment device (produced by Samco, Inc.)
  Water vapor: 2 mmol/min, electric power: 75 W, pressure: 40 Pa, distance between electrodes: 50 mm, treatment time: 20 min
Plasma Treatment (2): Carbon Tetrafluoride Plasma
  Device: BP-1 high-frequency plasma treatment device (produced by Samco Inc.)
  $CF_4$ gas: 5 ml/min, electric power: 75 W, pressure: 100 Pa, distance between electrodes: 50 mm, treatment time: 10 min
Plasma Treatment (3): Atmospheric-Pressure Plasma
  Device: Plasma-treatment system (produced by Rikaseiki Co., Ltd.)
  Gas: Dry air: 40 L/h, irradiation distance: 10 mm, treatment time: 400 m/s×10 times
Plasma Treatment (4): Atmospheric-Pressure Plasma
  Device: Tough plasma (produced by Fuji Machinery Co., Ltd.)
  Gas: $N_2$: 29.7 L/min+dry air: 0.3 L/min, irradiation distance: 10 mm, treatment time: 20 m/s×10 times
Plasma Treatment (5): Atmospheric-Pressure Plasma
  Device: Precise 300 C (produced by e-Square Co., Ltd.)
  Gas: $N_2$: 125/min+$H_2O$: 2 L/min, irradiation distance: 1 mm, treatment time: 1 m/s×10 times
Plasma Treatment (6): Atmospheric-Pressure Plasma
  Device: Precise 300 C (produced by e-Square Co., Ltd.)
  Gas: $N_2$: 125/min+$H_2$: 3.6 L/min, irradiation distance: 1 mm, treatment time: 1 m/s×10 times

Test Example 3

The color-changing layer of the indicator in Example 2, which was prepared using the ink composition of Example 2, was subjected to the same color change tests as in Test Example 2. Under all of plasma treatment conditions (1) to (6), the color change (color difference) ΔE*ab between before and after the treatment was confirmed to be 5 or more. Specifically, the results demonstrate that the completion of the plasma treatments can be confirmed.

Test Example 4

The color-changing layer of the indicator in Example 3, which was prepared using the ink composition of Example 3, was subjected to the same color change tests as in Test Example 2. Under all of plasma treatment conditions (1) to (6), the color change (color difference) ΔE*ab between before and after the treatment was confirmed to be 5 or more. Specifically, the results demonstrate that the completion of the plasma treatments can be confirmed.

Test Example 5

The color-changing layer of the indicator in Example 4, which was prepared using the ink composition of Example 4, was subjected to the same color change tests as in Test Example 2. Under all of plasma treatment conditions (1) to (6), the color change (color difference) ΔE*ab between before and after the treatment was confirmed to be 5 or more. Specifically, the results demonstrate that the completion of the plasma treatments can be confirmed.

The invention claimed is:

1. An ink composition for detecting plasma treatment comprising a colorant, a binder resin, and an extender, wherein the binder resin contains a phenolic resin and the extender is all or partially silica.

2. The ink composition according to claim 1, wherein the phenolic resin is at least one member selected from the group consisting of alkyl phenolic resins, terpene phenolic resins, and rosin-modified phenolic resins.

3. The ink composition according to claim 1, wherein the colorant is at least one member selected from the group consisting of anthraquinone colorants, methine colorants, azo colorants, phthalocyanine colorants, triphenylmethane colorants, and xanthene colorants.

4. The ink composition according to claim 1, comprising at least one member of nonionic surfactants or cationic surfactants.

5. The ink composition according to claim 1, comprising at least one colorant component that does not change color in a plasma treatment atmosphere.

6. The ink composition according to claim 2, wherein the colorant is at least one member selected from the group consisting of anthraquinone colorants, methine colorants, azo colorants, phthalocyanine colorants, triphenylmethane colorants, and xanthene colorants.

7. The ink composition according to claim 2, comprising at least one member of nonionic surfactants or cationic surfactants.

8. The ink composition according to claim 3, comprising at least one member of nonionic surfactants or cationic surfactants.

9. The ink composition according to claim 2, comprising at least one colorant component that does not change color in a plasma treatment atmosphere.

TABLE 1

| Formulation | | Example | | | | Comparative Example | | |
| --- | --- | --- | --- | --- | --- | --- | --- | --- |
| | | 1 | 2 | 3 | 4 | 1 | 2 | 3 |
| C.I. Disperse Red 167:1 (azo colorant) | | 0.1 | | 0.1 | 0.1 | 0.1 | | |
| C.I. Pigment Green 7 (phthalocyanine colorant) | | 0.4 | 0.4 | | | 0.4 | 0.4 | |
| C.I. Pigment Yellow 74 (azo colorant) | | | | 0.4 | 0.4 | | | 0.4 |
| C.I. Solvent: Blue 5 (triphenylmethane colorant) | | | 0.1 | | | | 0.1 | 0.1 |
| Shoka-men RS1/2 (nitrocellulose, produced by SNPE Japan K.K.) | | 10.0 | | 8.0 | | 10.0 | | 7.0 |
| Shoka-men RS7 (nitrocellulose, produced by SNPE Japan K.K.) | | | 8.0 | | | | 3.5 | |
| Tamanol 100S (alkylphenol, produced by Arakawa Chemical Industries, Ltd.) | | 2.5 | | | 10.0 | | | |
| YS Polystar U115 (terpenephenol, produced by Yasuhara Chemical Co., Ltd.) | | | 2.0 | | | | | |
| Tamanol 135 (rosin modified phenol, produced by Arakawa Chemical Industries, Ltd.) | | | | 2.5 | | | | |
| Versamid JP802 (polyamide, produced by BASF) | | | | | | | 7.1 | 3.5 |
| Cyclohexanone | | 12.4 | 12.4 | 11.1 | 11.1 | 12.4 | 12.4 | 12.4 |
| PM | | 1.4 | 1.4 | 1.4 | 1.4 | 1.4 | 1.4 | 1.4 |
| Butyl cellosolve | | 58.9 | 59.4 | 60.5 | 61.1 | 61.4 | 61.1 | 56.9 |
| Aerosil R-972 (silica, produced by Nippon Aerosil Co., Ltd.) | | 14.3 | 14.3 | 12.0 | 12.0 | 14.3 | 12.0 | 14.3 |
| Nikkol CA2580 (quaternary ammonium salt surfactant, produced by Nikko Chemicals Co., Ltd.) | | | 2.0 | | | | 2.0 | |
| PEG4000 (polyethylene glycol, produced by Sanyo Chemical Industries, Ltd.) | | | | 4.0 | 4.0 | | | 4.0 |
| Total | | 100.0 | 100.0 | 100.0 | 100.0 | 100.0 | 100.0 | 100.0 |
| Heat Resistance Test | Color change difference ΔE*ab between before and after treatment | 3 | 2 | 3 | 2 | 27 | 12 | 14 |
| Color Change Test | Color change difference ΔE*ab between before and after O2 plasma gas treatment | 26 | 22 | 20 | 20 | 38 | 34 | 36 |
| | Color change difference ΔE*ab between before and after Ar plasma gas treatment | 18 | 20 | 21 | 15 | 36 | 34 | 37 |

In the table, PM indicates propylene glycol monomethyl ether.

10. A plasma treatment detection indicator comprising a color-changing layer formed from the ink composition according to claim 1.

11. The indicator according to claim 10, comprising a non-color-changing layer that does not change color in a plasma treatment atmosphere.

12. A plasma treatment package comprising a gas-permeable package and the indicator according to claim 10 on the inner surface of the gas-permeable package.

13. The package according to claim 12, having a transparent window in a part of the package so as to enable the indicator to be checked from the outside.

14. A plasma treatment method comprising placing one or more articles to be treated in the package according to claim 12, sealing the package containing the one or more articles to be treated, and placing the package in a plasma treatment atmosphere.

15. The treatment method according to claim 14, wherein the package is placed in a plasma treatment atmosphere until the color-changing layer of the indicator changes color.

* * * * *